United States Patent
Blanck et al.

(10) Patent No.: US 11,986,351 B2
(45) Date of Patent: May 21, 2024

(54) FLEXIBLE ELECTRIC CIRCUIT FOR ULTRASOUND CATHETERS AND RELATED DEVICES AND METHODS

(71) Applicant: St. Jude Medical, Cardiology Division, Inc., St. Paul, MN (US)

(72) Inventors: Arthur G. Blanck, Ramona, CA (US); Fermin Armando Lupotti, Lake Forest, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 17/375,111

(22) Filed: Jul. 14, 2021

(65) Prior Publication Data
US 2022/0061808 A1 Mar. 3, 2022

Related U.S. Application Data

(60) Provisional application No. 63/071,763, filed on Aug. 28, 2020.

(51) Int. Cl.
*A61B 8/00* (2006.01)
*A61B 8/12* (2006.01)
(Continued)

(52) U.S. Cl.
CPC .............. *A61B 8/4494* (2013.01); *A61B 8/12* (2013.01); *H05K 3/4644* (2013.01); *H01B 7/0045* (2013.01)

(58) Field of Classification Search
CPC ...... A61B 18/1492; A61B 2017/00526; A61B 2018/00077; A61B 2018/00178;
(Continued)

(56) References Cited

U.S. PATENT DOCUMENTS 5,713,944 A * 2/1998 Kroll .................... A61N 1/0563
607/122
9,717,141 B1 7/2017 Tegg
(Continued)

FOREIGN PATENT DOCUMENTS

| CN | 209878830 U | 12/2019 |
|----|-------------|---------|
| EP | 2809236 B1 | 12/2019 |

(Continued)

OTHER PUBLICATIONS

International Search and Written Opinion issued in International Application No. PCT/US2021/041522, dated Nov. 9, 2021.

*Primary Examiner* — Minh N Trinh
(74) *Attorney, Agent, or Firm* — Wiley Rein LLP

(57) ABSTRACT

A flexible electronic circuit includes a plurality of leaves having a proximal section, a distal section, and an intermediate section. The plurality of leaves are bonded to each other within the distal section and loose within the intermediate section. The intermediate section also includes conductive connector pads for a wiring harness. A plurality of test connector pads are disposed on the plurality of leaves within the proximal section. The leaves within the proximal section may also be bonded to each other, for example in a ribbon or stepped configuration, in order to facilitate connection to testing apparatus. Once the circuit is tested, the proximal section can be severed from the intermediate section prior to installation of the circuit into a medical device, such as an intracardiac echocardiography catheter.

9 Claims, 4 Drawing Sheets

(51) Int. Cl.
*H01B 7/00* (2006.01)
*H05K 3/46* (2006.01)

(58) Field of Classification Search
CPC ........ A61B 8/12; A61B 8/445; H01B 7/0045; H05K 1/0268; H05K 1/0298; H05K 1/118; H05K 2201/0909
See application file for complete search history.

(56) References Cited

U.S. PATENT DOCUMENTS

| | | | |
|---|---|---|---|
| 9,962,223 B2 * | 5/2018 | Lindquist | ........... A61B 18/1492 |
| 2017/0042614 A1 | 2/2017 | Salahieh et al. | |
| 2018/0289356 A1 | 10/2018 | Buesseler et al. | |
| 2022/0061808 A1 * | 3/2022 | Blanck | ................. H05K 1/0268 |

FOREIGN PATENT DOCUMENTS

| | | | |
|---|---|---|---|
| WO | WO 0187412 A2 * | 11/2001 | |
| WO | 2016/039824 A1 | 3/2016 | |

* cited by examiner

FLEXIBLE ELECTRIC CIRCUIT FOR ULTRASOUND CATHETERS AND RELATED DEVICES AND METHODS

CROSS-REFERENCE TO RELATED APPLICATIONS

This application claims the benefit of U.S. provisional application No. 63/071,763, filed 28 Aug. 2020, which is hereby incorporated by reference as though fully set forth herein.

BACKGROUND

The present disclosure relates generally to catheters that are used in the human body. In particular, the present disclosure relates to a small form-factor flexible electronic circuit suitable for incorporation into an intravascular catheter, such as within the tip of such a catheter.

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart.

It is known to incorporate various electronic components into the tips of intravascular catheters. For instance, piezoelectric ultrasound transducers and supported electronics packages (implemented, for example, as an application-specific integrated circuit (ASIC) or field-programmable gate array (FPGA)) may be mounted within the tip of an intracardiac echocardiography (ICE) catheter, such as disclosed in United States patent application publication no. 2018/0289356 and U.S. provisional application No. 62/987,574, both of which are hereby incorporated by reference as though fully set forth herein. The relatively small size of such components, however, increases the complexity, and therefore the cost, of manufacture.

BRIEF SUMMARY

Disclosed herein is a flexible electronic circuit, including: a plurality of leaves having a proximal section, a distal section, and an intermediate section, wherein the plurality of leaves are bonded to each other within the distal section and loose within the intermediate section; a plurality of conductive connector pads disposed on the plurality of leaves within the intermediate section; and a plurality of test connector pads disposed on the plurality of leaves within the proximal section.

In embodiments of the disclosure, the plurality of leaves are bonded to each other within the proximal section. For example, they can be bonded to each other to form a stepped profile within the proximal section.

According to aspects of the disclosure, the plurality of leaves form a ribbon configuration within the proximal section.

The flexible electronic circuit can also include at least one of an ultrasound transducer array and an electronics package mounted to the plurality of leaves within the distal section.

Optionally, the flexible electronic circuit according can include a plurality of tooling alignment holes within the proximal section.

Also disclosed herein is a method of manufacturing a flexible electronic circuit, including the steps of: providing a plurality of leaves having a proximal section, a distal section, and an intermediate section, wherein the plurality of leaves are bonded to each other within the distal section and loose within the intermediate section; disposing a plurality of conductive connector pads on the plurality of leaves within the intermediate section; disposing a plurality of test connector pads on the plurality of leaves within the proximal section; and severing the proximal section from the intermediate section to create a plurality of flying leads from the loose leaves within the intermediate section.

At least one of an ultrasound transducer array and an electronics package can be mounted to the plurality of leaves within the distal section.

It is also contemplated that the method can include steps of: connecting the plurality of test connector pads to a testing apparatus and testing operability of the at least one of the ultrasound transducer array and the electronics package via the connected testing apparatus prior to severing the proximal section from the intermediate section.

The method can also include securing a wiring harness to the plurality of flying leads. For example, the method can include securing the wiring harness to the plurality of conductive connector pads disposed within the intermediate section of the plurality of leaves.

The plurality of leaves of the proximal section can be bonded into a stacked configuration. In embodiments of the disclosure, the stacked configuration has a stepped profile.

Alternatively, the plurality of leaves of the proximal section can be arranged into a ribbon configuration.

In aspects of the disclosure, the method further includes forming a plurality of tooling alignment holes in the plurality of leaves within the proximal section.

The instant disclosure also provides a flexible electronic circuit, including: a plurality of leaves having a proximal section, a distal section, and an intermediate section, wherein the plurality of leaves are bonded to each other within the proximal section and the distal section, and the plurality of leaves are loose within the intermediate section; a transducer package mounted to the plurality of leaves within the distal section; a plurality of conductive connector pads disposed on the plurality of leaves within the intermediate section; and a plurality of test connector pads disposed on the plurality of leaves within the proximal section.

Embodiments of the flexible electronic circuit further include a plurality of test tooling alignment holes in the plurality of leaves within the proximal section.

It is contemplated that the plurality of leaves within the proximal section may be bonded to each other in a stacked configuration, such as a stacked configuration having a stepped profile. Alternatively, the plurality of leaves within the proximal section may be bonded to each other in a ribbon configuration.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

Aspects of the instant disclosure relate to flexible electronic circuits suitable for use to connect electronics packages integrated into the distal ends of intravascular catheters (e.g., positioned within the distal tip assemblies of such catheters). Those of ordinary skill in the art will appreciate that the teachings herein can be applied to good advantage in connection with various types of catheters, including, but not limited to, intracardiac echocardiography (ICE) catheters, such as the ViewFlex™ Xtra ICE Catheter (Abbott Laboratories, Abbott Park, Illinois).

Figure 1:
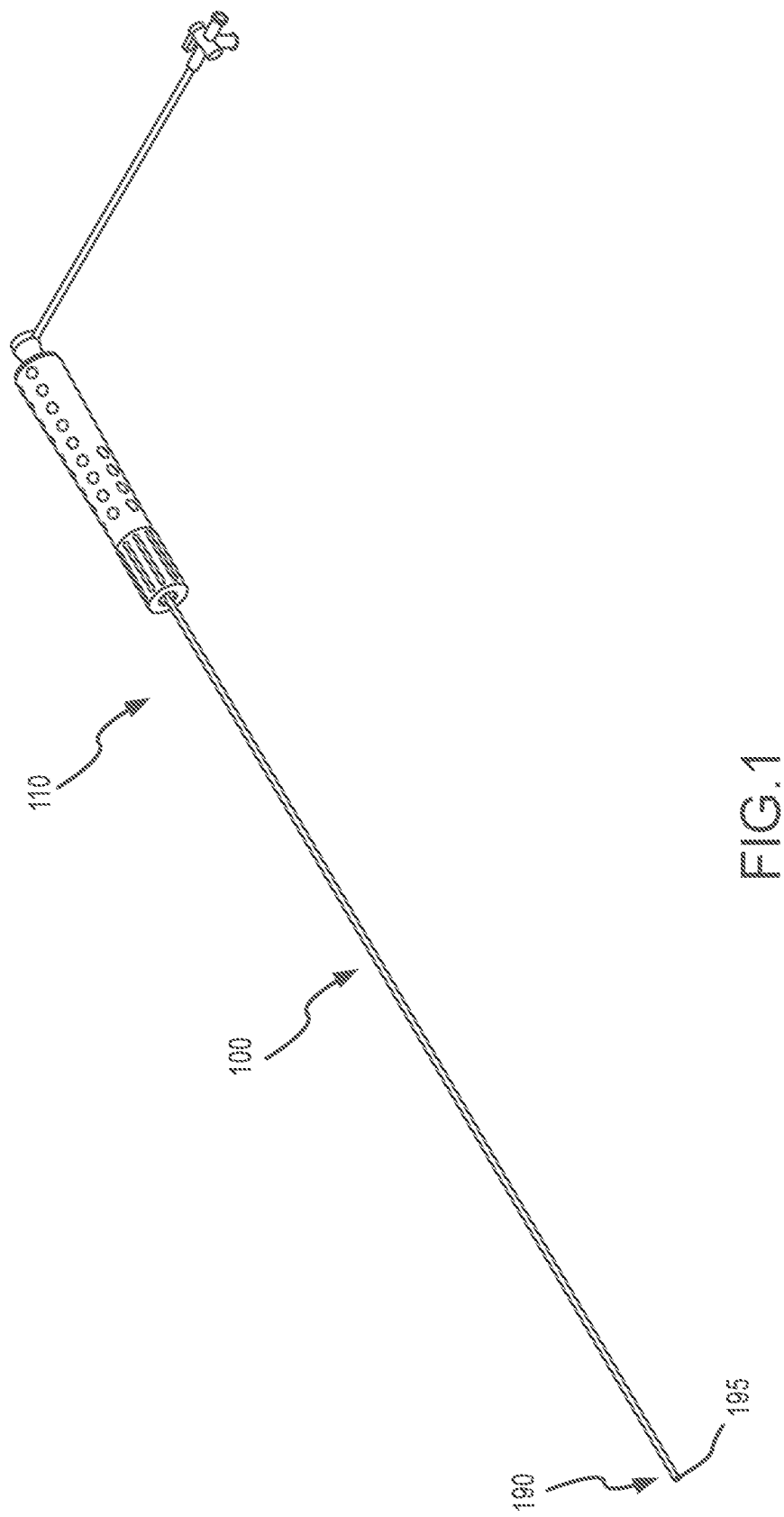
FIG. 1 is a perspective view of a representative catheter according to aspects of the instant disclosure.

For purposes of illustration, FIG. 1 depicts a perspective view of a representative catheter 100, including a shaft 105 having a proximal portion 110 and a distal portion 190, which terminates in a tip 195. Insofar as the basic construction of catheter 100 will be familiar to those of ordinary skill in the art, the details thereof will be omitted herein, except to the extent relevant to an understanding of the instant disclosure.

Figure 2:
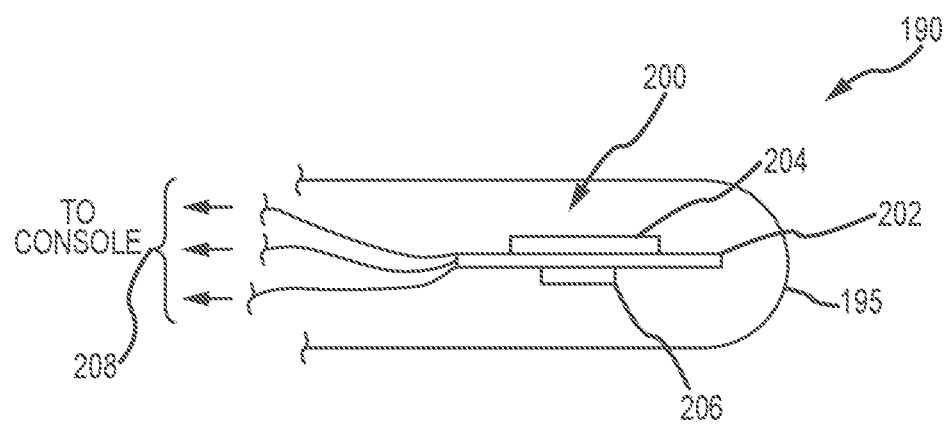
FIG. 2 schematically illustrates the distal region of the representative catheter of FIG. 1, including the interior of the tip portion.

FIG. 2 is a schematic representation of the interior of distal portion 190 of catheter 100, including tip 195. Tip 195 can include a flexible electronic circuit 200, including a flexible substrate 202 (which can be formed from a plurality of leaves according to the teachings herein) and a transducer package (e.g., ultrasound array 204 and electronics package 206) mounted to substrate 202. A wiring harness 208, including a plurality of wires, interconnects flexible electronic circuit 200 to an external device, such as an ultrasound imaging console. Only three wires are shown within wiring harness 208, but it should be understood that this is merely exemplary and that more or fewer wires may be used in a device according to the present teachings.

Figure 3:
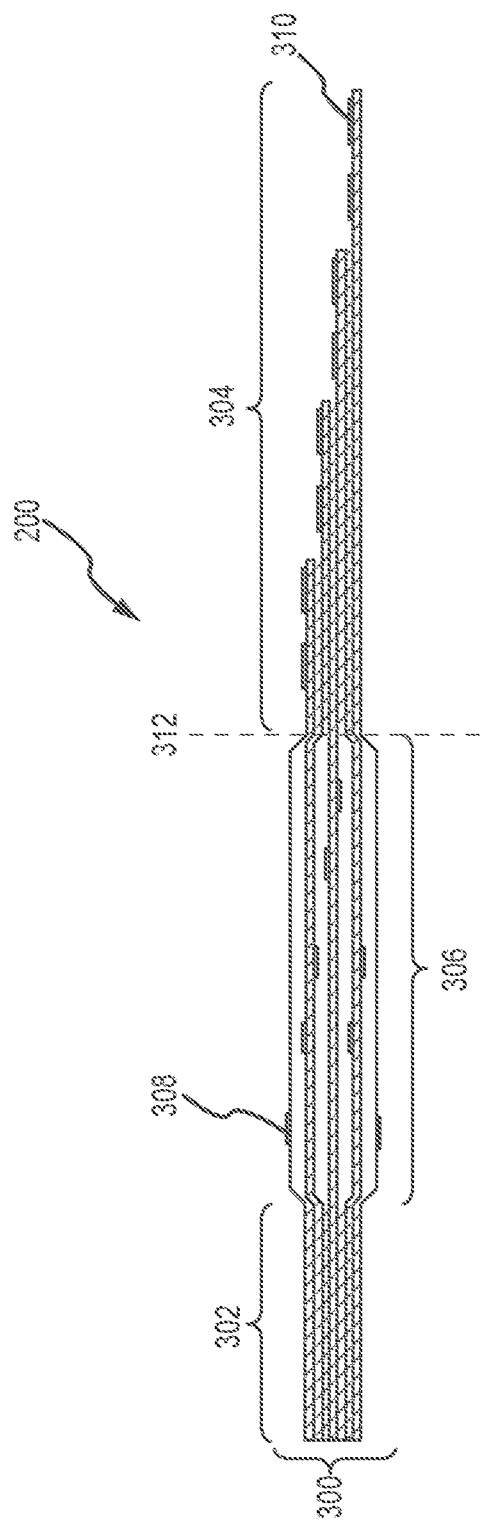
FIG. 3 depicts a first embodiment of a flexible circuit according to the instant disclosure.

FIG. 3 depicts a first embodiment of flexible electronic circuit 200. As shown in FIG. 3, flexible electronic circuit includes a plurality of leaves 300. Seven leaves are shown in FIG. 3, but this number is merely exemplary; more or fewer leaves may be used in a device according to the present teachings.

Each leaf 300 has a distal section 302, a proximal section 304, and an intermediate section 306. Within distal section 302, leaves 300 are bonded to each other (e.g., through the use of thermosetting adhesives as part of a laminating process), such as in the stacked arrangement shown in FIG. 3, to provide substrate 202 upon which a transducer package can be mounted (the transducer package, which is visible in FIG. 2, is omitted from FIG. 3 for the sake of clarity of illustration). Those of ordinary skill in the art will also be familiar with techniques suitable for applying conductive traces to leaves 300 within distal section 302 as part of substrate 202.

Conversely, within intermediate section 306, leaves 300 are loose and have disposed thereon a plurality of conductive connector pads 308. As used herein, the term "loose" means not bonded to each other; thus, within intermediate section 306, leaves 300 are not bonded to each other, and can therefore be referred to as "loose leaves" or a "loose leaf configuration." Moreover, because leaves 300 are not bonded to each other within intermediate section 306, intermediate section 306 forms a plurality of flying leads to which the wires of wiring harness 208 may be secured.

Of course, conductive connector pads 308 are also conductively coupled into distal section 302, so as to carry signals, such as power and communications signals, to and from the transducer package. Insofar as conductive coupling between the attachment point for a wiring harness and a transducer package will be familiar to those of ordinary skill in the art, it need not be further described herein.

Leaves 300 are also bonded within proximal section 304 in order to form a convenient coupon portion to connect flexible circuit 200 to testing equipment during manufacture. In the embodiment of flexible circuit 200 depicted in FIG. 3, leaves 300 are bonded into a stack having a stepped profile within proximal section 304.

A plurality of test connector pads 310, which are ultimately conductively coupled into distal section 302 and the transducer package mounted therein, are disposed on leaves 300 within proximal section 304. The use of a stepped profile within proximal section 304 simplifies the conductive connection between test connector pads 310 and distal section 302, in particular by reducing the need to create vias through leaves 300 that are "higher" in the stack in order to conductively couple to leaves 300 that are "lower" in the stack.

It is contemplated, however, to bond leaves 300 within proximal section without creating the stepped profile, in which case test connector pads 310 could all be placed on the "upper" surface of the stack, all on the "lower" surface of the stack, or distributed between both the "upper" and "lower" surfaces of the stack. It should be recognized that distributing test connector pads 310 onto both the "upper" and "lower" surfaces would also reduce the need to create vias through leaves 300, though not to the extent as the stepped profile shown in FIG. 3.

Because leaves 300 are bonded to each other within proximal section 304, the location of and spacing between test connector pads 310 is known and substantially (that is, within the margins permitted by the flexing of leaves 300) fixed. This simplifies proof testing of flexible circuit 200 during manufacture by ensuring that a plurality of testing probes can be attached to test connector pads 310, and thus conductively coupled to the transducer package within distal section 302, quickly and reliably, without the need for special tooling or alignment and connection on a probe-by-probe basis, as would be necessary were leaves 300 loose within proximal section 304.

To further simplify testing and facilitate proper alignment with testing apparatus, additional datums can be provided within proximal portion 304. For instance, in embodiments of the disclosure, leaves 300 can include one or more alignment holes within proximal portion 304, which mate with corresponding protrusions on a testing apparatus to ensure proper alignment to test connector pads 310.

Figure 4:
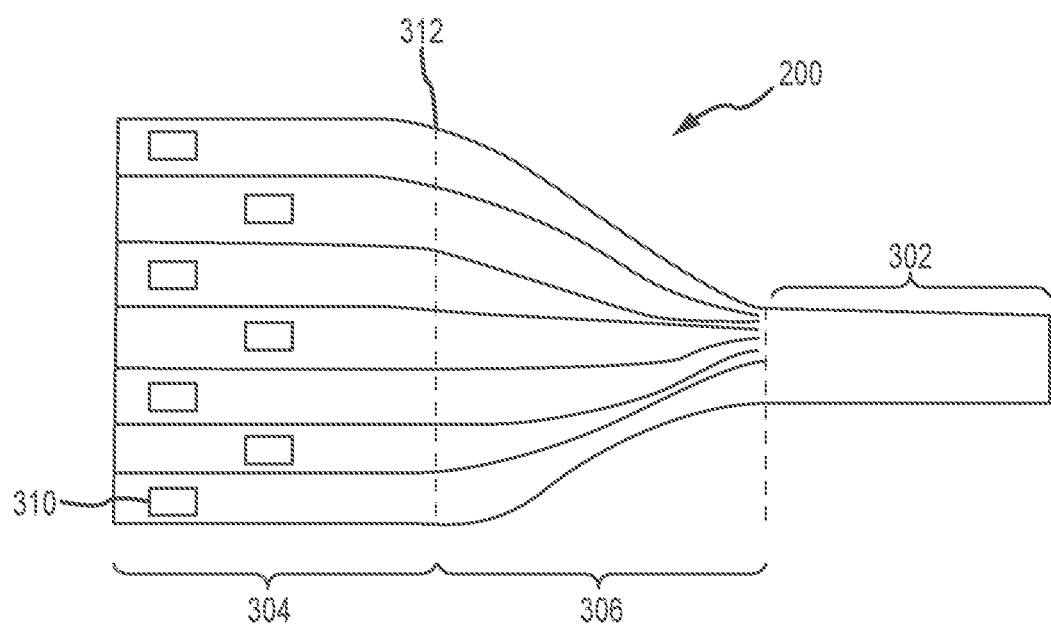
FIG. 4 depicts a second embodiment of a flexible circuit according to the instant disclosure.

FIG. 4 depicts a second embodiment of flexible electronic circuit 200. In the embodiment of FIG. 4, as in the embodiment of FIG. 3, leaves 300 are bonded to each other in a stack within distal section 302 and loose within intermediate section 306. In proximal section 304, however, leaves 300 are fanned out and arranged in a ribbon configuration for insertion into one or more flexible printed circuit (FPC) connectors, which can, in turn, be connected to testing apparatus. Optionally, leaves 300 can be bonded to each other in the ribbon configuration, so as to facilitate insertion into a single FPC connector.

Like the stepped profile described above, the ribbon configuration reduces the need to create vias through leaves 300, and indeed may entirely eliminate the need to do so. On the other hand, it may require leaves 300 to be individually inserted into FPC connectors, though this is still likely simpler manufacturing process than individually connecting each test connector pad 310 to a corresponding test probe.

Once testing is complete and the functionality of flexible circuit 200 is verified, proximal section 304 can be severed (e.g., along cut-line 312 in FIGS. 3 and 4), leaving the flying leads of intermediate section 306 as the most proximal section of flexible circuit 200. Flexible circuit 200 can be installed into tip 195 of catheter 100, with wiring harness 208 secured to conductive connector pads 308.

Although several embodiments have been described above with a certain degree of particularity, those skilled in the art could make numerous alterations to the disclosed embodiments without departing from the spirit or scope of this invention.

For example, rather than using individual wires, wiring harness 208 could utilize one or more long flex and/or printed circuits.

Other configurations of leaves 300 within proximal section 304 are also contemplated. For instance half of leaves 300 could be formed into a first stack as described above, and the remainder of leaves 300 could be formed into a second stack as described, with the two stacks placed side-by-side analogous to the ribbon configuration described above.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of manufacturing a flexible electronic circuit, the method comprising:
    providing a plurality of leaves having a proximal section, a distal section, and an intermediate section, wherein the plurality of leaves are bonded to each other within the distal section and loose within the intermediate section;
    disposing a plurality of conductive connector pads on the plurality of leaves within the intermediate section;
    disposing a plurality of test connector pads on the plurality of leaves within the proximal section; and
    severing the proximal section from the intermediate section to create a plurality of flying leads from the loose leaves within the intermediate section.

2. The method according to claim 1, further comprising mounting at least one of an ultrasound transducer array and an electronics package to the plurality of leaves within the distal section.

3. The method according to claim 2, further comprising:
    connecting the plurality of test connector pads to a testing apparatus; and
    testing operability of the at least one of the ultrasound transducer array and the electronics package via the connected testing apparatus, prior to severing the proximal section from the intermediate section.

4. The method according to claim 1, further comprising:
    providing a wiring harness; and
    securing the wiring harness to the plurality of flying leads.

5. The method according to claim 4, wherein securing the wiring harness to the plurality of flying leads comprises securing the wiring harness to the plurality of conductive connector pads disposed within the intermediate section of the plurality of leaves.

6. The method according to claim 1, further comprising bonding the proximal section of the plurality of leaves into a stacked configuration.

7. The method according to claim 4, wherein the stacked configuration of the proximal section of the plurality of leaves has a stepped profile.

8. The method according to claim 1, further comprising arranging the proximal section of the plurality of leaves into a ribbon configuration.

9. The method according to claim 1, further comprising forming a plurality of tooling alignment holes in the plurality of leaves within the proximal section.

* * * * *